(12) United States Patent
Roggan et al.

(10) Patent No.: US 8,333,760 B2
(45) Date of Patent: Dec. 18, 2012

(54) HIGH FREQUENCY GENERATOR FOR ELECTROSURGICAL CUTTING

(75) Inventors: André Roggan, Berlin (DE); Timo Strauss, Berlin (DE)

(73) Assignee: Celon AG Medical Instruments (DE)

( * ) Notice: Subject to any disclaimer, the term of this patent is extended or adjusted under 35 U.S.C. 154(b) by 652 days.

(21) Appl. No.: 12/490,526

(22) Filed: Jun. 24, 2009

(65) Prior Publication Data

US 2009/0275938 A1 Nov. 5, 2009

Related U.S. Application Data

(63) Continuation of application No. PCT/EP2009/002429, filed on Mar. 27, 2009, and a continuation-in-part of application No. PCT/EP2009/050043, filed on Jan. 5, 2009.

(30) Foreign Application Priority Data

Jan. 3, 2008 (DE) .................. 10 2008 003 475

(51) Int. Cl.
*A61B 18/10* (2006.01)

(52) U.S. Cl. ............... 606/34; 606/32; 606/33; 606/37; 606/38; 606/39

(58) Field of Classification Search ............... 606/32–42
See application file for complete search history.

(56) References Cited

U.S. PATENT DOCUMENTS

| | | | | |
|---|---|---|---|---|
| 4,209,018 A * | 6/1980 | Meinke et al. | .............. | 606/40 |
| 4,271,837 A * | 6/1981 | Schuler | .............. | 606/39 |
| 4,658,815 A | 4/1987 | Farin et al. | .............. | 128/303.14 |
| 4,818,954 A * | 4/1989 | Flachenecker et al. | ........ | 331/183 |
| 5,108,391 A * | 4/1992 | Flachenecker et al. | ......... | 606/38 |
| 5,540,682 A | 7/1996 | Gardner et al. | .............. | 606/37 |
| 2002/0019596 A1* | 2/2002 | Eggers et al. | .............. | 600/564 |
| 2004/0030329 A1* | 2/2004 | Hagg | .............. | 606/38 |
| 2004/0097914 A1* | 5/2004 | Pantera et al. | .............. | 606/34 |

(Continued)

FOREIGN PATENT DOCUMENTS

DE 29 46 728 5/1981

(Continued)

OTHER PUBLICATIONS

International Search Reported mailed Dec. 29, 2009 in corresponding International Application No. PCT/EP2009/002429 (in English language).

*Primary Examiner* — Michael Peffley
*Assistant Examiner* — Khadijeh Vahdat
(74) *Attorney, Agent, or Firm* — Ostrolenk Faber LLP

(57) ABSTRACT

A high frequency generator connected to an electrosurgical instrument comprising an electrical output terminal, a power source electrically connected to the output terminal, an arc detector, and a power control for controlling the electrical power delivered through the output terminal. The power control initially causes the delivery of a high output power for a phase for initial cutting support and thereafter, if ignition of an arc has occurred for a predetermined period of time to cause the delivery of reduced or no power and subsequently for a predetermined period of time to cause the delivery of reduced or no power at which no arc occurs, or if no ignition of an arc has occurred during the phase for initial cutting support, to cause the delivery of reduced or no power for a predetermined period of time of a short pause interval.

12 Claims, 4 Drawing Sheets

Therein
T1: initial cutting support
T2: shortened coagulation or pause interval
T3: cutting phase with ignited arc
T4: prolonged coagulatin or pause interval

U.S. PATENT DOCUMENTS

2004/0172017 A1* 9/2004 Marion et al. .................. 606/37
2005/0119646 A1* 6/2005 Scholl et al. .................... 606/32
2009/0082765 A1* 3/2009 Collins et al. .................. 606/38

FOREIGN PATENT DOCUMENTS

| DE | 32 28 136 | 2/1984 |
| --- | --- | --- |
| DE | 34 20 340 | 12/1984 |
| DE | 35 15 622 | 11/1986 |
| DE | 35 30 335 | 3/1987 |
| DE | 36 22 337 | 1/1988 |
| DE | 41 26 609 | 2/1993 |
| DE | 41 35 185 | 4/1993 |
| DE | 195 00 219 | 7/1995 |
| EP | 1 849 425 | 10/2007 |
| WO | WO 02/11634 | 2/2002 |

* cited by examiner

Therein
T1: initial cutting support
T2: shortened coagulation or pause interval
T3: cutting phase with ignited arc
T4: prolonged coagulatin or pause interval

HIGH FREQUENCY GENERATOR FOR ELECTROSURGICAL CUTTING

CROSS-REFERENCE TO RELATED APPLICATIONS

This application is a continuation of PCT International Application No. PCT/EP2009/002429, filed Mar. 27, 2009, the content of which is incorporated herein by reference. This application is also a continuation-in-part of PCT International Application No. PCT/EP2009/050043, filed Jan. 5, 2009, which claims priority to German Application No. 10 2008 003 475.4, filed Jan. 3, 2008, the contents of which are incorporated herein by reference.

BACKGROUND OF THE INVENTION

The invention concerns a high frequency generator for the connection of an electrosurgical instrument for cutting body tissue by means of an arc.

High frequency generators of that kind usually have an electrical output terminal to which an electrosurgical instrument can be connected and an input terminal by way of which it can be connected to a current or voltage source. In that case power control serves for controlling the electrical power delivered by way of the output terminal.

Devices of that kind are basically already known from for example DE 195 00 219, DE 41 35 185, DE 41 26 609, DE 36 22 337, DE 34 20 340, DE 29 46 728, DE 35 30 335 or DE 32 28 136.

SUMMARY OF THE INVENTION

In electrosurgical cutting, in particular in the case of endoscopic interventions or in polypectomy, there is the danger that the respective electrosurgical cutting electrode being used penetrates into the tissue to an excessive depth because the operator cannot sufficiently sensitively guide the electrosurgical instrument.

To reduce that risk and to permit electrosurgical cutting guidance which is as controlled as possible known high frequency generators have a cyclically implemented power delivery when providing the electrical power required for electrosurgical cutting. That cyclic power delivery involves cutting intervals which are comparatively short in terms of time and which involve a relatively high level of electrical power, and comparatively long coagulation or pause intervals in which no or a low level of electrical power is delivered.

High frequency generators designed for electrosurgical cutting instruments generally have initial cutting assistance or support, that is to say to produce an arc firstly a very high level of power is delivered in order to rapidly dry out the body tissue bearing against the cutting electrode, and thereby rapidly to achieve a high tissue impedance necessary to produce an arc and thus the voltage required for firing the arc. Thereafter the power can be reduced, with the arc being maintained. In actual fact the arc can never be permanently maintained with an applied ac voltage, but at the latest collapses at each zero crossing of the ac voltage. What is meant however in regard to the term which is also used hereinafter, 'maintaining the arc', is that the tissue drying which is achieved means that the impedance (and therewith also the voltage) remain so high that, in each period of the ac voltage, the peak voltage reaches the value required for igniting an arc.

At the beginning of application of the high frequency current however, the excessively low impedance means that ignition of an arc does not happen straightaway so that initial cutting support is appropriate. Such initial cutting support is appropriate in particular when using cutting electrodes of large area such as for example polypectomy snare loops in order to permit the large area to dry out quickly and thus to ensure a rapid initial cutting characteristic.

Particularly in the case of endoscopic mucosal resection (EMR) or polypectomy, because of the large-area snare loop cutting electrodes, it is often not possible to achieve the high impedance required for ignition of an arc with only one pulse with a high electrical power level for initial cutting support because the thermal energy introduced into the tissue is not sufficient to increase the impedance and therewith also the voltage in the region of the cutting electrode to such an extent that an arc can be ignited.

For that reason in known high frequency generators the power delivery is implemented cyclically in accordance with a fixed pulse sequence:

Firstly an initial cutting pulse is delivered, involving a very high power, and then, when the arc ignites, a pulse of reduced power is produced to maintain the arc, and finally a pause interval.

The length of the pause interval is in that case so selected that the surgical instrument, as already described, can be guided in more controlled fashion. It is precisely when for example with large-area electrodes a large number of initial cut-supporting pulses is required in order to ignite an arc that the waiting time required for that purpose can be perceived by the operator as being a nuisance. The object of the invention is to provide a high frequency generator of the kind set forth in the opening part of this specification, which provides a better initial cut characteristic.

In accordance with the invention that object is attained by a high frequency generator of the kind set forth in the opening part of this specification which has an arc detector and a power control which is so adapted that initially for a phase for initial cutting support it causes the delivery of a high output power for initial cutting support and subsequently thereto either if ignition of an arc has occurred during the phase for initial cutting support, for a predetermined period of time of a cutting phase it causes the delivery of a power which is reduced in relation to the high power and subsequently for a predetermined period of time of a long pause interval it causes the delivery of no power or a low power at which no arc occurs, or if no ignition of an arc has occurred until the attainment of a predetermined maximum duration of the phase for initial cutting support it causes the delivery of no power or a low power for a predetermined period of time of a short pause interval.

The invention is based on the realisation that, for the situation where no arc has been ignited, a long pause or coagulation interval is not required and can therefore lead to unnecessary waiting times during the course of the treatment.

An important advantage enjoyed by the high frequency generator according to the invention over the state of the art is that the time which elapses until first ignition of the arc is shortened in comparison with high frequency generators in the state of the art.

More specifically high frequency generators in the state of the art provide a constant sequence of initially a phase for initial cutting support, then a cutting phase, and lastly a pause or coagulation interval, in which respect the presence of an arc has no influence on the length of the pause or coagulation interval.

In the case of the high frequency generator according to the invention the power delivered during the initial cutting support phase and the power delivered during the cutting phase and the power delivered during the coagulation or pause interval preferably respectively corresponds approximately to those powers which are already known from the state of the art. Suitable frequencies for the individual phases are also to be found in the state of the art.

Preferably the maximum power in the initial cutting support phase is about 500 watts and during the cutting phase it is preferably about 250 watts. The preferred frequency in that respect is preferably between 300 kHz and 2 MHz.

Preferably the predetermined maximum duration of the initial cutting support phase is about 50 ms. Preferably the predetermined period of time for the cutting phase is about 15 ms.

A typical period of time for the long coagulation or pause interval following a cutting phase is about 500-1000 ms while a suitable period of time for the short coagulation or pause interval directly following the initial cutting support phase (without cutting phase as no arc was ignited) is about 100-400 ms.

Besides the high frequency generator just disclosed the invention also concerns a method of electrosurgical cutting of body tissue, wherein the method firstly provides the application of a high frequency current with a high power during an initial cutting support phase (wherein application of the high power takes place at most for the period of time of a predetermined maximum duration) and subsequently thereto either application of a high frequency current at a power which is reduced in comparison with the high power for a predetermined period of time of a cutting phase and subsequently thereto the application of a low or no power for the period of time of a predetermined long pause or coagulation interval if ignition of an arc has occurred during the application of the high frequency current at high power, or application of a high frequency current of a low or no power for a predetermined period of time of a short pause or coagulation interval if no ignition of an arc has occurred during application of the high frequency current at high power.

As the method according to the invention corresponds to an electrosurgical treatment of patients using the high frequency generator according to the invention the surgical use of the different variants of the high frequency generator according to the invention represents different variants of the method.

BRIEF DESCRIPTION OF THE DRAWINGS

An embodiment of the invention will now be described in greater detail with reference to FIGS. 1 to 4 in which.

DETAILED DESCRIPTION OF THE INVENTION

Figure 1:
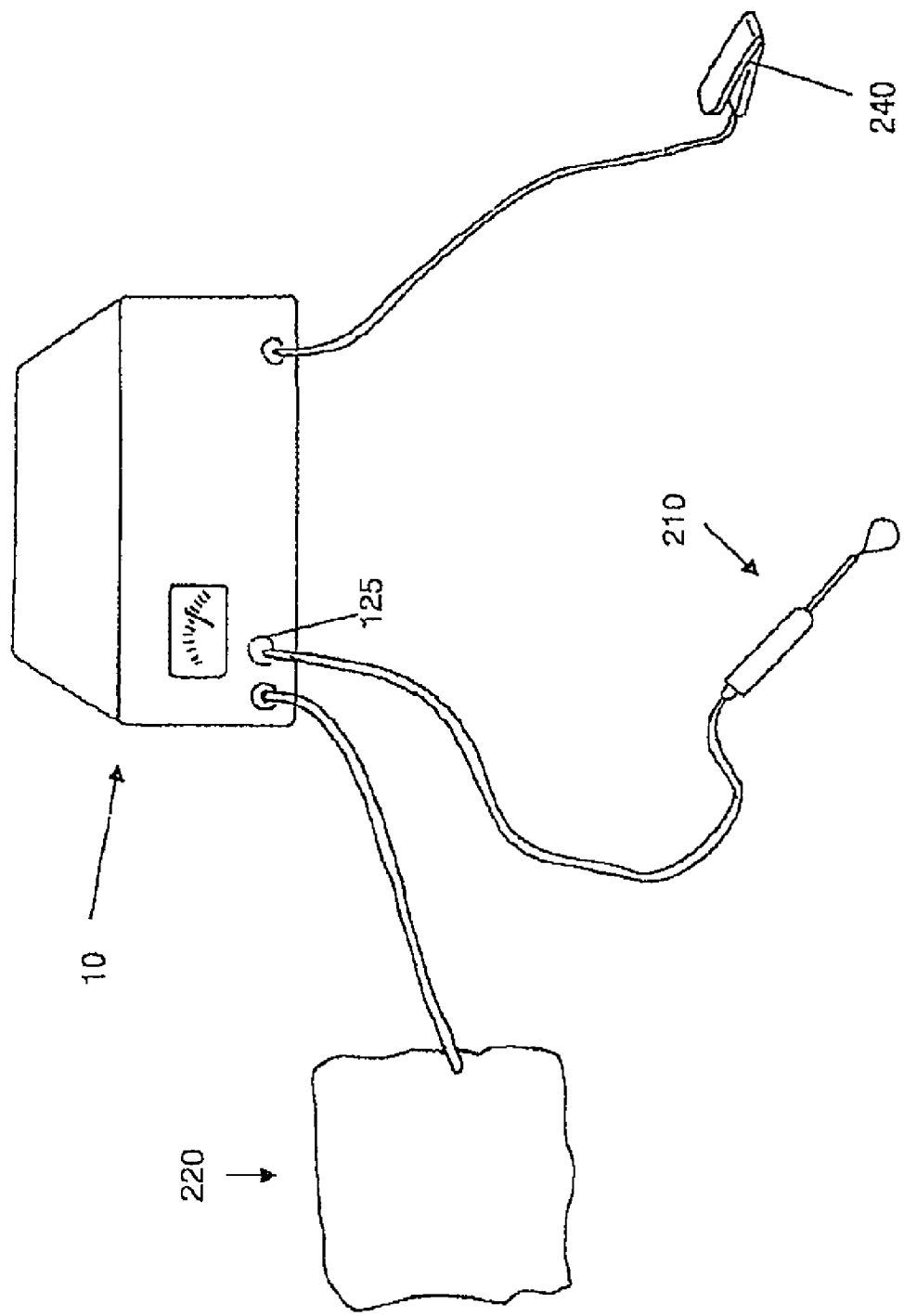
FIG. 1 shows a high frequency generator with a connected electrical instrument.

FIG. 1 shows a high frequency generator 10 provided at the input side with a power cable for connection to a public mains system. The high frequency generator 10 is connected to a foot switch 240 serving to switch the high frequency generator 10 on and off. On the output side two output poles 125 of the high frequency generator 10 are connected by way of current lines to an electrode 210 of an electrosurgical instrument and a neutral electrode 220. The electrosurgical instrument in this case has a cutting electrode 210 which in the embodiment by way of example as shown in FIG. 1 is in the form of a snare loop cutting instrument.

Figure 2:
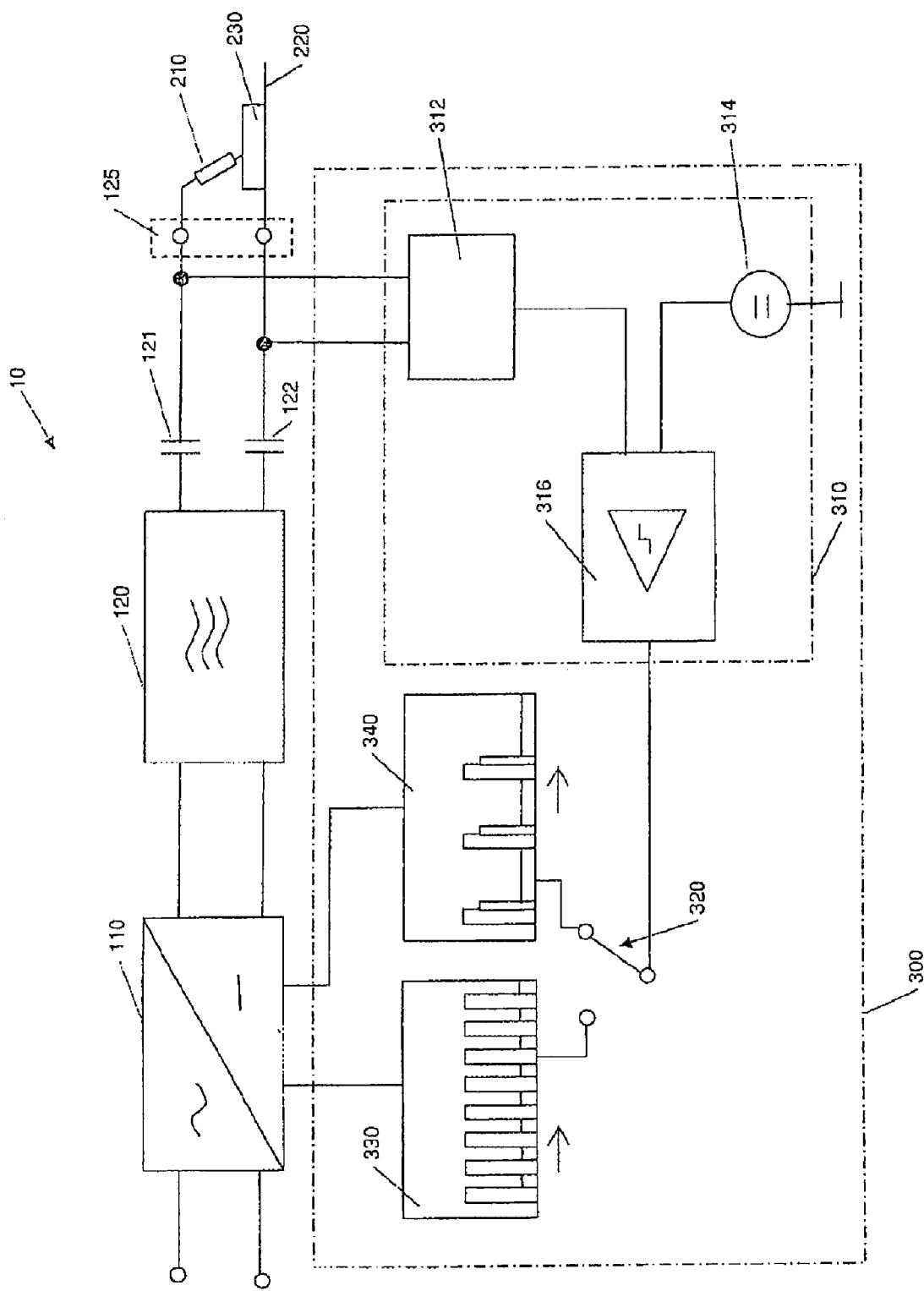
FIG. 2 shows a circuit diagram illustrating the principle of the high frequency generator.

FIG. 2 shows a circuit diagram illustrating the principle of a preferred embodiment of the high frequency generator according to the invention with an initial cutting performance which is improved over the state of the art. The illustrated embodiment is in particular also suitable for surgical interventions in the field of endoscopic mucosal resection (EMR) and polypectomy.

The high frequency generator 10 includes a clock-controllable power supply unit 110 which can be connected at the input side to the public ac supply mains and which at the output side is connected to the input of a high frequency generator module 120. The power supply unit 110 converts an ac voltage into a dc voltage which can be clock-controlled by means of at least one clock in such a way that pulse sequences involving pulses of different pulse lengths and of different pulse amplitudes are available at the output of the power supply unit 110. In other words the power delivery of the power supply unit 110 is clock-controlled and a succession of different power levels is outputted for the respective length of a corresponding time interval. The high frequency generator module 120 converts the dc voltage into an ac voltage at a frequency of between 0.3 and 2 MHz. The output of the high frequency generator module 120 is connected by way of two antifaradisation capacitors 121, 122 and by way of a two-pole electrical output terminal 125 of the high frequency generator 10 to an electrode 210 of an electrosurgical instrument and a neutral electrode 220. The two antifaradisation capacitors are intended to prevent the transmission of dangerous direct currents which occur upon ignition of an arc between the electrode 210 and tissue 230, to the patient.

The electrosurgical instrument generally comprises a cutting electrode 210 and a handle. In order to be able to electrosurgically cut tissue in the proximity of the cutting electrode 210 an arc must be produced between the electrode 210 and the body tissue. That is effected by a direct current of high electrical power, which is clock-controlled by means of at least one clock, being outputted at the output of the power supply unit 110 to the input of the high frequency generator module 120. Thereupon the high frequency generator module 120 outputs for the same period of time a high frequency current, that is to say high frequency alternating current, of high electrical power. The cutting electrode 210 of the electrosurgical instrument and the neutral electrode 220 are connected to the output of the high frequency generator module 120 by way of the two-pole electrical output terminal 125. Heating of the tissue 230 bearing against the cutting electrode 210 and thus rapid drying-out thereof are effected by the high frequency current outputted to the electrodes 210 and 220. As a result the impedance of the body tissue rises in the proximity of the electrode 210 and the voltage required for ignition of the arc is achieved. It is only with that arc that the operator is in a position to carry out a desired cut in the tissue 230 against the cutting electrode 210.

To maintain the arc required for electrosurgical cutting after a previously successfully ignited arc, a comparatively lower level of electrical power is sufficient.

Switching over from the high ignition power level to a lower power level for maintaining the arc is effected for example by a power control 300 which is disposed in the high frequency generator 10 and which includes an arc detector 310, a change-over switch 320, a first clock 330 and a second clock 340.

The arc detector 310 in turn includes an arc sensor 312, a reference signal source 314 and a comparator 316. The inputs of the arc sensor 312, as inputs of the arc detector 310, are connected at the output side downstream of the antifaradisation capacitors 121 and 122 to the poles of the high frequency generator module 120 and detect the presence of an arc. In that case the output of the arc sensor 312 is connected to the input of the comparator 316. The output of the reference signal source 314 is also connected to the input of the comparator 316. The output of the comparator 316, as the output of the arc detector 310, is connected to the input of the change-over switch 320, the two outputs of which are connected to the two clocks 330 and 340. The change-over switch 320 activates the clock 330 or 340 in dependence on the output signal of the arc detector 310.

The outputs of the clocks 330 and 340 are at the same time the outputs of the power control 300. The clock 330 causes the power supply unit to output direct current at a high power level (for initial cutting support) and to output direct current at a low power level for short pause intervals therebetween. No power may also be outputted in the pause interval.

The clock 340 causes the power supply unit to output direct current at a high power level (for initial cutting support) and—immediately thereafter, after ignition of the arc—to output direct current at a lower power level for maintaining the arc and finally to output direct current at a low power level for long pause intervals. In this case also alternatively no power may be outputted in the pause interval.

To detect the arc the arc sensor 310 detects for example a dc voltage applied across the electrodes 210 and 220. As a dc voltage measured there is a function of the rectified current at the cutting location, which is caused when cutting with a high frequency current, the arc detector 310 can thereby detect the presence of an arc. Arc detection on the basis of a dc voltage which is produced is known from DE 28 01 833.

The arc detector 310 can however also be adapted to analyse the spectral power distribution of the output of the generator 10 and in that case to compare two different frequency ranges to each other. The production of an arc can also be detected by an analysis of the 'higher harmonics'. The use of 'higher harmonics' is described in this context in greater detail in DE 41 26 607 A1.

As an alternative thereto the arc detector 310 can also be adapted to detect the presence of an arc by means of a photooptical element as the arc sensor 312. Such a detector is proposed in DE 25 04 280.

Arc detection can also be effected by the detection of a sudden change in impedance. In general terms the arc detector 310 can be designed in any desired fashion to detect the presence of an arc.

At any event the sensor 312 outputs a signal proportional to the measurement value, to the input of the comparator 316. The comparator 316 compares that output signal to the reference signal which is also at the input of the comparator 316 and which is outputted by the reference signal source 314. Comparison of the two values establishes whether an arc has been ignited at the electrosurgical instrument.

It will be appreciated that the individual components listed here of the arc detector 310 can also be embodied in a programmable microcontroller.

When an arc is present the arc detector 310 outputs a representative signal. That is shown in greater detail in relation to FIG. 4.

When no arc has occurred at the electrode 210 of the electrosurgical instrument then the arc detector 310 switches the change-over switch 320 to the first clock 330 for initial cutting support in order to prevent an unnecessarily long pause or coagulation interval and to reduce the time until ignition of an arc occurs.

When however an arc has occurred at the electrosurgical instrument then the arc detector 310 switches the change-over switch 320 over to the second clock 340 to implement a long pause or coagulation interval which is now necessary. In that case the clocks 330 and 340 of the power control 340 provide for clock control of the dc voltage output of the power supply unit 110 in such a way that the above-mentioned pulse sequences are outputted at the output of the power supply unit 110.

The power control 300 can also be entirely or partially implemented in a microcontroller in which the components 310, 320, 330 and 340 are programmed.

Figure 3:
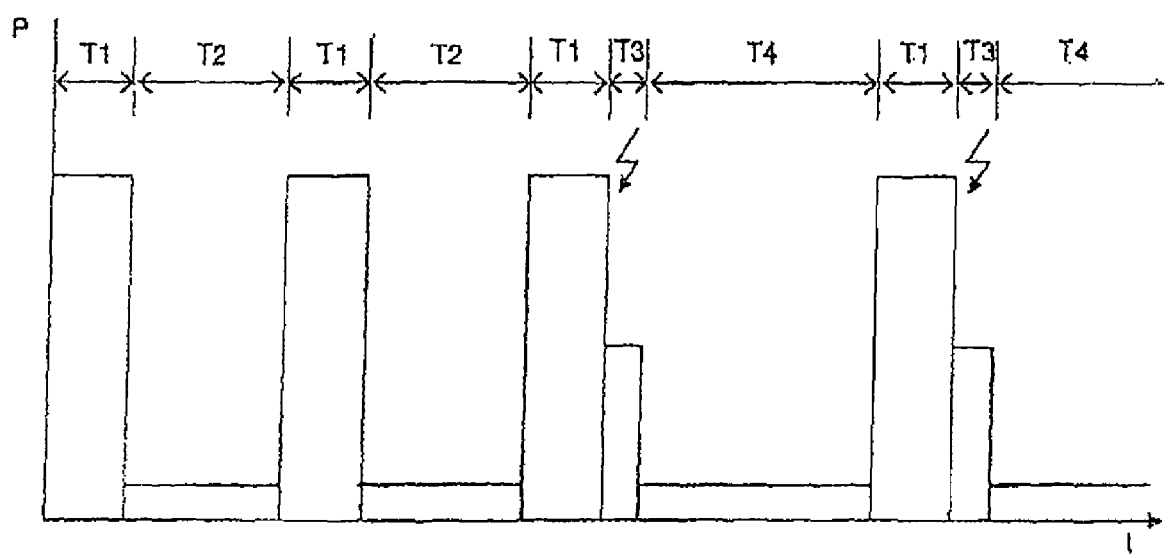
FIG. 3 shows an example of a pulse diagram of the pulse sequences outputted at the output of the high frequency generator.

The power delivered by the high frequency generator 10 to the electrode 210 of the electrosurgical instrument is shown in detail in FIG. 3 in a pulse diagram.

The time sequence shown in FIG. 3 begins as soon as the physician actuates the foot switch 240 by depressing it. The foot switch 240 remains depressed until the end of the application.

The time intervals T1 which are shown in the pulse diagram and which involve a high power level P1 serve for initial cutting support. If the impedance of the tissue 230 is still not sufficient, that is to say the tissue 230 is not yet sufficiently dried out, the time interval T1 is followed by a time interval T2 as a shortened coagulation or pulse interval involving a low power level P3. The time intervals T1 and T2 can be repeated a plurality of times until an arc is ignited.

If ignition of an arc is detected during or after a time interval T1 a time interval T3 immediately follows. The time interval T3 is a cutting interval and serves to maintain an arc which was previously successfully ignited in the time interval T1, and has a lower power level than the time interval T1 because a lower power level is sufficient to maintain the arc. The time interval T3 is followed by a time interval T4 as a prolonged coagulation or pause interval involving a markedly lower power level P3. The time intervals T1, T3 and T4 are repeated as long as the cutting operation in the tissue 230 lasts, that is to say as long as the physician actuates the foot switch 240.

Figure 4:
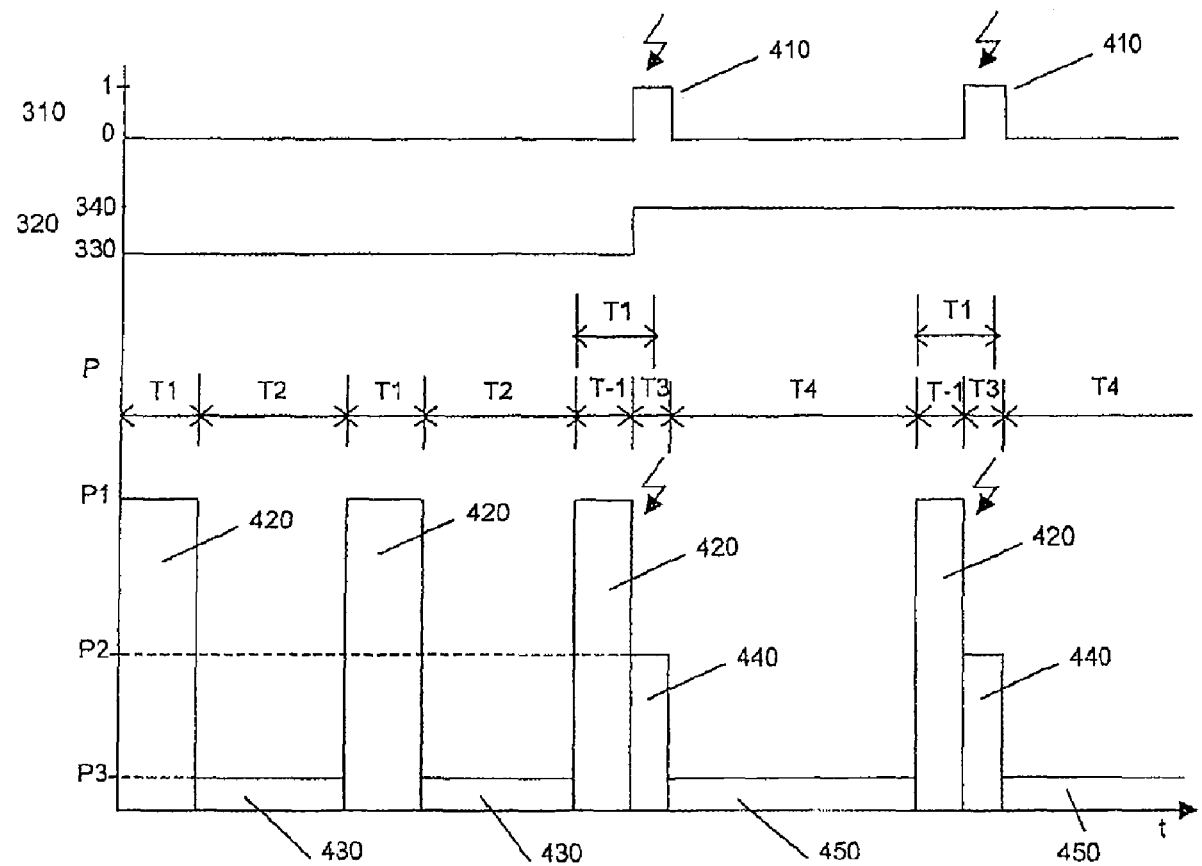
FIG. 4 shows an example of a further pulse diagram.

FIG. 4 shows a further pulse diagram for a high frequency generator 10 according to the invention. It shows signals from the HF generator 10 during an application such as for example polypectomy which the physician starts, for example by actuation of the foot switch 240. FIG. 4, besides the power P delivered by the HF generator 10, also illustrates the output of an arc signal 410 from the arc detector 310 and the switching position of the change-over switch 320.

At the beginning of the application, as shown in FIG. 3, a high power P1 is delivered in an initial cutting support phase 420. The maximum duration T1 is predetermined for the initial cutting support phase 420. As no arc is ignited in the procedure illustrated by way of example during the first two initial cutting support phases 420, as in FIG. 3, the high power P1 occurs until the end of the maximum duration T1. At the beginning of the application the arc detector 310 does not deliver a signal or at least not a signal representative of the existence of an arc. In the pulse diagram in FIG. 4 that is represented by the value 0. In addition the change-over switch 320 actuates the clock 330 at the beginning of the application.

The initial cutting support phase 420 is followed by the short pause interval 430 after the expiry of the maximum duration T1, as in FIG. 3, for a predetermined short pause time T2. In the short pause interval 430 the HF generator delivers a lower level of power P3. The lower power P3 can even be so low that it is substantially equal to zero. After the end of the short pause interval 430 an initial cutting support phase 420 is again effected, as already described with reference to FIG. 3. Initial cutting support phases 420 and short pause intervals 430 alternate as long as no arc is ignited and the arc detector 310 thus does not output a signal representative of the presence of an arc.

In the application by way of example in FIG. 4 an arc ignites during the third initial cutting support phase 420. The arc detector 310 outputs the arc signal 410 representative of the presence of the arc. In FIG. 4 that is represented for example by the signal value 1.

When the arc signal 410 occurs the initial cutting support phase 420 ends immediately and there then follows a cutting phase 420 at reduced power P2, which is suitable for maintaining the arc. As shown in FIG. 4 the reduced power P2 is higher than the low power P3 but lower than the high power P1. The initial cutting support phase 420 ends as soon as the arc signal 410 occurs after a time T-1 which can be shorter than the maximum duration T1. The cutting phase 420 is of a predetermined time duration T3.

After the end of the cutting phase 440 there now follows the long pause interval 450 involving a long pause time T4 because, with the occurrence of the arc signal 410, the change-over switch 320 switched over from the clock 330 to the clock 340. With the end of the cutting phase 440 the arc is extinguished and there is thus no arc signal 410. Nonetheless the clock 340 remains activated by the change-over switch 320. At the end of the long pause time T4 there again follows an initial cutting support phase 420, during which an arc is again ignited. The moment in the initial cutting support phase 420 at which the arc ignites can vary. Therefore the duration T-1 of the initial cutting support phase 420 can also vary.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. A high frequency generator, for electrical connection to an electrosurgical instrument configured for igniting an arc, comprising:
an electrical output terminal for connection to the electrosurgical instrument,
a current or voltage source electrically connected to the electrical output terminal,
an arc detector, and
a power control configured for controlling electrical power delivered through the electrical output terminal to the electrosurgical instrument,
wherein the power control is configured to:
initially cause delivery of a high output power (P1) to the electrosurgical instrument during an initial cutting support phase for a first predetermined maximum period of time (T1), in which the arc detector is configured to deliver an arc signal, if an arc has ignited at the electrosurgical instrument, and subsequently thereto:
if no arc signal was outputted until attainment of the first predetermined maximum period of time (T1) to cause delivery of no power or a lower power (P3) for a second predetermined period of time (T2) of a short pause interval at which no arc occurs, and subsequently to deliver the high power (P1) to the electrosurgical instrument again for the first predetermined maximum period of time (T1), in which the arc detector is configured to deliver the arc signal, if the arc has ignited at the electrosurgical instrument, and
if the arc signal was outputted during the initial cutting support phase to cause the high output power (P1) to reduce to a second power (P2) to thereby maintain the arc and enter a cutting phase configured to cut a targeted tissue for a third predetermined period of time (T3) and subsequently, to cause delivery of no power or lower power (P3) for a fourth predetermined period of time (T4) of a long pause interval, at which no arc occurs.

2. The high frequency generator according to claim 1 wherein the power control is configured so that time duration of the long pause interval is between 500 and 1000 ms and time duration of the short pause interval is between 100 and 400 ms.

3. The high frequency generator according to claim 2 wherein the power control is configured so that the third predetermined period of time (T3) of the cutting phase is between 10-20 ms.

4. The high frequency generator according to claim 3 wherein the power control is configured so that the time duration of the cutting phase is 15 ms.

5. The high frequency generator according to claim 1 wherein the power control is configured so that the third predetermined period of time (T3) of the cutting phase is between 10-20 ms.

6. The high frequency generator according to claim 5 wherein the power control is configured so that the time duration of the cutting phase is 15 ms.

7. The high frequency generator according to claim 1 wherein the power control is configured so that the phase for initial cutting support ends and goes into the cutting phase, when the arc detector detects the ignition of the arc.

8. The high frequency generator according to claim 7 wherein the arc detector is configured so that it detects the ignition of the arc by detection of a dc voltage.

9. The high frequency generator according to claim 1 wherein the arc detector is configured to detect the ignition of the arc from a characteristic configuration of higher harmonics thereof.

10. The high frequency generator according to claim 1 wherein the power control is configured so that the first predetermined maximum period of time (T1) of the initial cutting support phase is up to 50 ms.

11. The high frequency generator according to claim 1 wherein at least one of the first predetermined maximum period of time (T1) for the initial cutting support, the third predetermined period of time (T3) of the cutting phase, time duration of the long pause interval, and time duration of the short pause interval is adjustable.

12. The high frequency generator according to claim 1 wherein at least one of the high power (P1) of the phase for initial cutting support, the second power(P2) of the cutting phase, no power or the lower power (P3) of the long pause interval, and no power or the lower power (P3) of the short pause interval is adjustable.

* * * * *